(12) United States Patent
Huebner et al.

(10) Patent No.: US 7,498,575 B2
(45) Date of Patent: Mar. 3, 2009

(54) OPTICAL ANALYSIS DEVICE

(75) Inventors: Joerg Huebner, Dortmund (DE);
Rainer Krage, Herdecke (DE)

(73) Assignee: GFG Gesellschaft für Gerätebau mbH, Dortmund (DE)

( * ) Notice: Subject to any disclaimer, the term of this patent is extended or adjusted under 35 U.S.C. 154(b) by 270 days.

(21) Appl. No.: 11/426,065

(22) Filed: Jun. 23, 2006

(65) Prior Publication Data
US 2007/0007449 A1    Jan. 11, 2007

(30) Foreign Application Priority Data
Jun. 23, 2005  (DE) ........................ 10 2005 029 601
Jul. 6, 2005   (DE) ........................ 10 2005 031 857

(51) Int. Cl.
*G01J 5/00* (2006.01)
(52) U.S. Cl. .................................................. 250/338.1
(58) Field of Classification Search ... 250/338.1–338.5, 250/339.01–339.15
See application file for complete search history.

(56) References Cited

U.S. PATENT DOCUMENTS 3,875,408 A  *  4/1975  Pusch ...................... 250/338.1
5,428,222 A  *  6/1995  Alexay ...................... 250/343
5,451,787 A  *  9/1995  Taylor ...................... 250/338.5
5,578,818 A  *  11/1996 Kain et al. ................. 250/234
5,923,035 A     7/1999  Winkler et al.
7,268,881 B2 *  9/2007  Larsen et al. ............... 356/436
2003/0059153 A1* 3/2003  Miller et al. ................. 385/17
2004/0232338 A1* 11/2004 Tolton et al. ............. 250/338.5

FOREIGN PATENT DOCUMENTS

DE    44 37 188 A1    4/1996

* cited by examiner

*Primary Examiner*—David P Porta
*Assistant Examiner*—Kiho Kim
(74) *Attorney, Agent, or Firm*—David S. Safran; Roberts Mlotkowski Safran & Cole, P.C.

(57) ABSTRACT

An optical analysis device having a gastight housing, a radiation-permeable housing element, at least a first radiation source and associated first reflector and a second radiation source and associated second reflector, at least first and second detectors, and an external reflector. The radiation sources and the detectors are located within the housing, an absorption space being formed between the external reflector and the radiation-permeable housing element. A measurement beam emitted by the first radiation source and the first reflector, after reflection on the external reflector, re-enters the housing. A reference beam is emitted by the second radiation source and the second reflector. The measurement beam, after crossing the absorption space, is guided from the measurement beam reflector directly onto the first detector and the second detector and the reference beam from the second radiation source is directly incident on the first detector and the second detector.

16 Claims, 4 Drawing Sheets

OPTICAL ANALYSIS DEVICE

BACKGROUND OF THE INVENTION

1. Field of the Invention

The invention relates to an optical analysis device according to the principle of radiation absorption with a housing with at least one radiation-permeable housing element, with at least a first radiation source and a first reflector assigned to it and a second radiation source and a second reflector assigned to it, with at least a first detector and a second detector and with an external reflector located outside the housing, the radiation sources and the detectors being located within the housing, an absorption space being formed by the external reflector and the radiation-permeable housing element, a measurement beam emitted by the first radiation source and the first reflector after reflection on the external reflector re-entering the housing, and a reference beam being emitted by the second radiation source and the second reflector.

2. Description of Related Art

Optical analysis devices of the type under consideration have long been known in various embodiments and exploit the effect of radiation absorption by matter which is penetrated by electromagnetic radiation. The electromagnetic radiation is generally broadband and covers at least the frequency range in which the substance to be detected acts to absorb radiation. Each substance to be detected shows a characteristic absorption spectrum which is characterized in that the emitted electromagnetic radiation, after passing through the absorption space in which the substance to be detected is located, is relatively strongly attenuated in certain, generally narrowband absorption regions relative to the radiated power of adjacent frequency ranges. While the substances present can be identified via recording of an absorption spectrum, it is also possible to draw conclusions about certain concentrations of the substance via the intensity of the relative attenuation in the absorption range.

Nondispersive infrared analysis is used especially for the detection of gases and does not involve spectral decomposition of the emitted electromagnetic radiation. For nondispersive spectrometers, selective detectors are used which are sensitive only in a limited radiation range, specifically in the range in which the substance to be detected absorbs radiation. The selectivity of the filters used is often dictated by the interference filters connected upstream of the detectors. The detectors are generally pyroelectric detectors or thermocouples interconnected to form thermopiles.

It can be easily imagined that, when using only one detector, almost no conclusions can be drawn about the actual concentration of the substance which is to be detected, if it is possible for attenuation of the measurement means to be caused in some other way, for example, by the presence of interfering gases and other contaminants in the absorption space. To the same degree, for example, ageing-induced intensity attenuation of the radiation source also cannot be detected with only one detector. To compensate for these effects, use of at least two detectors is therefore known in the prior art, of which one detector is sensitive in the absorption range of the substance to be detected and the other detector is sensitive in the frequency range in which absorption by other substances is not possible (reference detector and measurement detector). Certain effects which adulterate the measurement can be compensated for by the signal obtained from the measurement detector being referenced to the detector obtained from the reference detector.

For example, it is known that the radiation emitted by the radiation source can be divided by mirrors into a measurement beam and a reference beam, the measurement beam and the reference beam being detected by two different detectors. By using only one radiation source, for example, the sensitivity drift of individual detectors—for example, caused by ageing or temperature dependency—cannot be compensated for, and thus, has an effect on the final measurement signal (German Patent DE 44 37 188 C2).

German Patent DE 197 13 928 C1 and corresponding U.S. Pat. No. 5,923,035 disclose an optical analysis device of the type under consideration, in which there is a beam splitter in the housing which deflects or transmits both the measurement beam and also the reference beam partially in the direction of the first detector and of the second detector. Between the beam splitter and the first detector and the second detector, a respective concentrator is connected which is used to homogenize the measurement beam or reference beam. On the one hand, it is disadvantageous in this construction that the beam splitter can cause temperature-dependent asymmetrical intensity distributions or intensity losses in the measurement and reference beam which become part of the measurement signal in a manner which cannot be compensated. Furthermore, by using concentrators, the angle of incidence of the measurement and reference beam on the respective downstream detector or on the interference filter upstream of the detector is necessarily reduced, by which its bandpass characteristic becomes more broadband, and thus, less gas-specific. Moreover, both the measurement beam and also the reference beam are greatly attenuated by a plurality of reflections; this has an adverse effect on the sensitivity of the optical analysis device.

One underlying problem in the use of optical analysis devices of the type under consideration here is that the spectral absorption capacity of substances is very different in its absorption range. Some gases absorb only very weakly and only in a very narrow wavelength range. In order to achieve good detection sensitivity, for only weakly absorbing components compared to more strongly absorbing components a longer absorption distance is necessary to obtain comparable signals at the same concentration of the substance. Simple matching of the known optical analysis devices to substances which absorb in different degrees or to different sensitivity ranges is not easily possible in the analysis devices underlying the invention.

SUMMARY OF THE INVENTION

A primary object of this invention is, therefore, to embody and develop an optical analysis device based on the principle of radiation absorption such that the aforementioned disadvantages are at least partially avoided.

The optical analysis device in accordance with the invention in which the aforementioned object is achieved is, first of all, essentially characterized in that the measurement beam, after passing through the absorption space, is guided directly to the first detector and the second detector by the measurement beam reflector located in the housing and the reference beam from the second radiation source and the second reflector is directly incident on the first detector and the second detector. The special configuration of the analysis device in accordance with the invention obviates the need to use a beam splitter within the housing; this makes construction altogether simpler and more cost-effective, and moreover, prevents the occurrence of temperature-dependent asymmetrical intensity losses by a beam splitter.

There are a host of possibilities for embodying and developing the teaching of the invention, for which reference is made to the dependent claims. The special configurations of the invention are addressed by the following remarks.

In one preferred exemplary embodiment of the optical analysis device in accordance with the invention, the measurement beam reflector is annular, certain regions of the measurement beam reflector reflecting certain portions of the measurement beam onto certain detectors. Therefore, it is possible for the part of the measurement beam reflected from the first region of the measurement beam reflector to contribute only to the irradiation of the first detector and another region of the measurement beam reflector to deflect another part of the measurement beam solely onto the second detector.

In another preferred exemplary embodiment, the surface of the measurement beam reflector is made to mix and homogenize the beam so that measurement beams reflected essentially from any region of the measurement beam reflector are guided onto the existing detectors and distributed. This has the especially advantageous effect that, even without an additional optically active element (concentrator, diffuser), thorough mixing of the different portions of the measurement beam is caused. Thus, local disruptions of the measurement beam act not only on a detector, but on all detectors so that asymmetrical influences on the measurement beam can be averaged out. In one especially advantageous exemplary embodiment, the radiation-mixing and radiation-homogenizing effect is caused by concave and/or convex microstructuring of the surface.

In another especially preferred exemplary embodiment of the optical analysis device in accordance with the invention, the distance of the external reflector from the housing can be adjusted. This measure can increase the absorption space such that the distance to be traversed in the absorption space by the measurement beam is increased. In this way, it is very easily possible to adapt the analysis device in accordance with the invention to substances which absorb to varying degrees so that operation of the optical analysis device in an optimum sensitivity range is possible. In another preferred exemplary embodiment of the analysis device, it is provided that the beam path of the measurement beam can be adjusted. This means that the focusing or broadening of the measurement beam can be varied so that the illumination of the detectors can be influenced.

The feature of adjustability of the measurement beam in conjunction with the distance adjustability of the external reflector from the housing is especially advantageous, but not necessary. By the coordinated interaction of the two adjustment possibilities the possibly overly wide fanning of the measurement beam when the distance of the external reflector from the housing increases can be counteracted by greater focusing of the measurement beam and vice versa. In one especially preferred exemplary embodiment, the adjustability of the beam path of the measurement beam is caused by shifting the first radiation source relative to the first reflector. By moving the first beam source along the optical axis of the first reflector, especially out of the focal point of the reflector, fanning of the measurement beam symmetrical to the optical axis is achieved, assuming that the reflector itself is made symmetrical. By moving the first radiation source out of the optical axis, inclination of the measurement beam relative to the optical axis of the reflector can also be accomplished.

In particular, there are various possibilities for embodying and developing the optical analysis device in accordance with the invention. In this regard, reference is made to the description of preferred exemplary embodiments below in conjunction with the figures of the accompanying drawings.

DETAILED DESCRIPTION OF THE INVENTION

Figure 1:
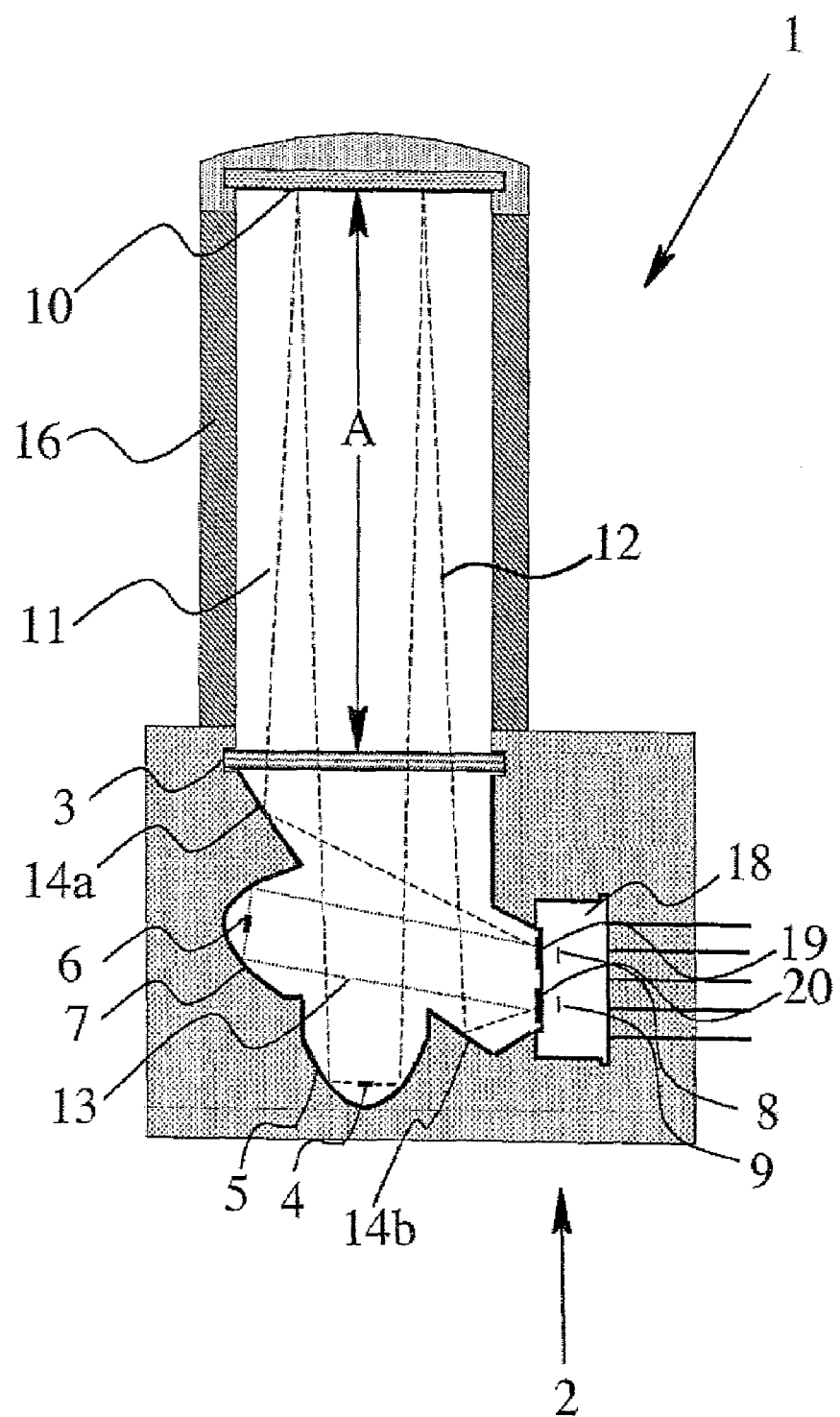
FIG. 1 is a sectional view of a preferred exemplary embodiment of the optical analysis device in accordance with the invention.

FIG. 1 shows a preferred embodiment of an optical analysis device 1 in accordance with the invention which has a gastight housing 2 with a radiation-permeable housing element 3. The radiation-permeable housing element 3 is essentially permeable to the radiation emitted from the first radiation source 4 so that the radiation emitted by the first radiation source 4 can leave the housing 2 on one side. The first radiation source 4 is assigned a first reflector 5 which is made parabolic in the exemplary embodiment shown in FIG. 1 so that a certain focusing of the radiation emitted by the first radiation source 4 is possible by it. In the gastight housing 2, there is also a second radiation source 6 with a second reflector 7 assigned to it. A first detector 8 and a second detector 9 which are sensitive to the radiation emitted by the first radiation source 4 and the second radiation source 6 are also located in the housing 2. In the specific case of the exemplary embodiment shown in FIG. 1, the first detector 8 and the second detector 9 are each a pyroelectric detector which is sensitive to the infrared range of electromagnetic radiation. The described optical analysis device is accordingly a non-dispersive infrared analyzer (NDIR).

Spaced apart from the gastight housing 2 or the radiation-permeable housing element 3, there is an external reflector 10 which reflects the radiation emitted from the first radiation source 4 such that it is reflected back through the radiation-permeable housing element 3 into the gastight housing 2. The external reflector 10, in the exemplary embodiment as shown in FIG. 1, is a planar mirror. The external reflector 10 and the radiation-permeable housing element 3 at least partially surround an absorption space 11. Gaseous, liquid or even solid samples of the substance which are to be tested for the presence and concentration of certain components of the substance are introduced into the absorption space 1. The analysis device 1 shown in FIG. 1 is used for spectrometric study of gaseous samples. However, basically, the invention is in no way limited to detection of gaseous substances.

By interaction with the first reflector 5, the first radiation source 4 emits a directed measurement beam 12 which leaves the housing interior through the radiation-permeable housing element 3 and is reflected back from the external reflector 10 into the gastight housing 2 by the radiation-permeable housing element 3. The measurement beam 12 consequently crosses the absorption space 11 twice. In interaction with the second reflector 7, the second radiation source 6 emits a reference beam 13 which does not leave the gastight housing 2.

In accordance with the invention, it is provided that the measurement beam 12 which returns from the absorption space 11 through the radiation-permeable housing element 3 to the gastight housing 2 is guided from the measurement beam reflector 14a, 14b located in the housing 2 directly onto the first detector 8 and the second detector 9, and that the reference beam 13 from the second radiation source 6 and the second reflector 7 is likewise directly incident on the first detector 8 and the second detector 9. Here, it is important that the measurement beam 12, after a one-time reflection on the measurement beam reflector 14a, 14b, and the reference beam 13 after one-time reflection on the second reflector 7 are directly incident on the detectors 8, 9, therefore, without interposition of other optically active elements. This extraordinarily simple construction, in particular, avoids the disadvantages which arise from the use of additional optical elements such as, for example, beam splitters by which additional intensity losses and temperature-dependent asymmetrical intensity distributions of the measurement beam 12 and of the reference beam 13 can result.

In the preferred exemplary embodiment shown in FIG. 1, the measurement beam reflector 14a, 14b, is annular, only the upper section edge and the lower section edge being visible in the cross section shown in FIG. 1. In this exemplary embodiment, the annular measurement beam reflector 14a, 14b, is made as a segment of a paraboloid such that the components of the measurement beam 12 incident on various areas of the measurement beam reflector 14a, 14b, are reflected in the direction to the detectors 8, 9.

A relatively smooth surface of the measurement beam reflector 14a, 14b, causes the portions of the measurement beam 12 which have been reflected from the first region of the measurement beam reflector 14a, 14b, to be reflected essentially to the first detector and the portions of the measurement beam 12 which are incident on another region of the measurement beam reflector 14a, 14b, to be reflected onto the second detector 9. This is disadvantageous when different regions of the measurement beam 12 are influenced to different degrees, whether by sample concentrations of varied strength or by asymmetrical fouling of the optical surfaces in the absorption space 11. These effects cannot be compensated by using a reference beam 13. However, the problem can be addressed with the preferred exemplary embodiment of the configuration of the measurement beam reflector 14a, 14b, shown in FIG. 2.

Figure 2:
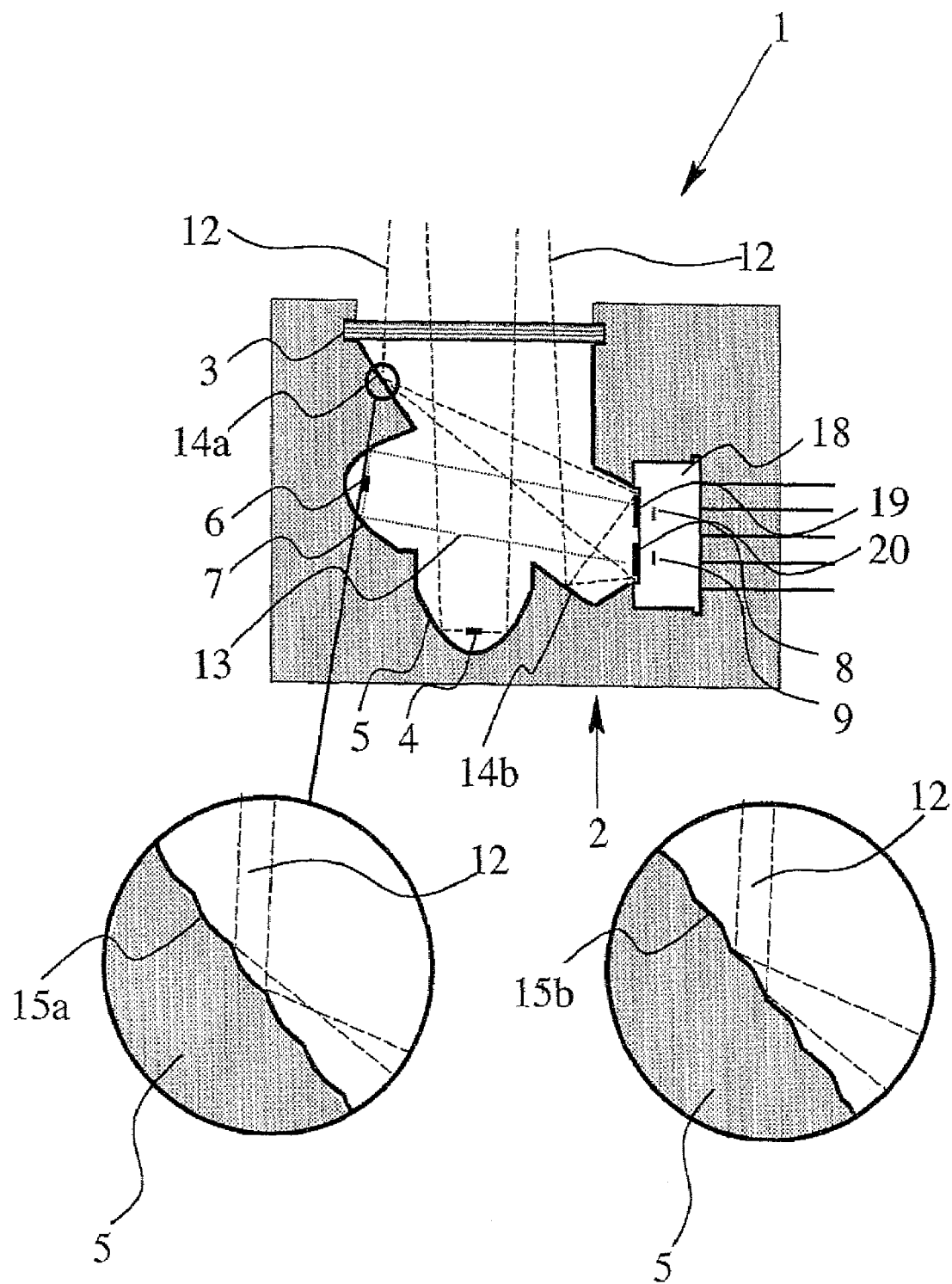
FIG. 2 is a section of another preferred embodiment of the optical analysis device in accordance with the invention with enlarged detail views of a surface area.

In particular, the enlarged details extracted in FIG. 2 show a construction in which the surface of the measurement beam reflector 14a, 14b, has either a concave microstructuring 15a (detail on the left) or a convex microstructuring 15b (detail on the right). The microstructurings 15a, 15b, of the measurement beam reflector 14a, 14b are made such that the measurement beam reflector 14a, 14b, acts to mix and homogenize the reflected measurement beams 12. Beam mixing does not take place randomly, but such that the parts of the measurement beams 12 reflected by a certain region of the measurement beam reflector 14a, 14b are widened essentially onto all detectors 8, 9, but not beyond. This ensures that for a spatially nonuniform influence on the measurement beams 12, the likewise nonhomogeneous intensity distribution resulting therefrom acts on one of the detectors 8, 9, not only to cause errors, but the error acts essentially equally on the two detectors 8, 9, and thus, can be compensated in the known manner.

In the preferred exemplary embodiment shown in FIG. 1, the distance A of the external reflector 10 from the housing 2 or from the radiation-permeable housing element 3 is adjustable. In the exemplary embodiment shown in FIG. 1, different distances A can be produced by the replacement of spacers 16, by which the distance A of interest is fixed. Because the extension of the absorption space 11 in the propagation direction of the measurement beam 12 is variable, the optical analysis device 1 can be adapted to substances which absorb to varying degrees, and therefore, it is possible to adapt the analysis device 1 in the optimum manner to the measurement range of the detectors 8, 9.

Figures 3A, 3B:
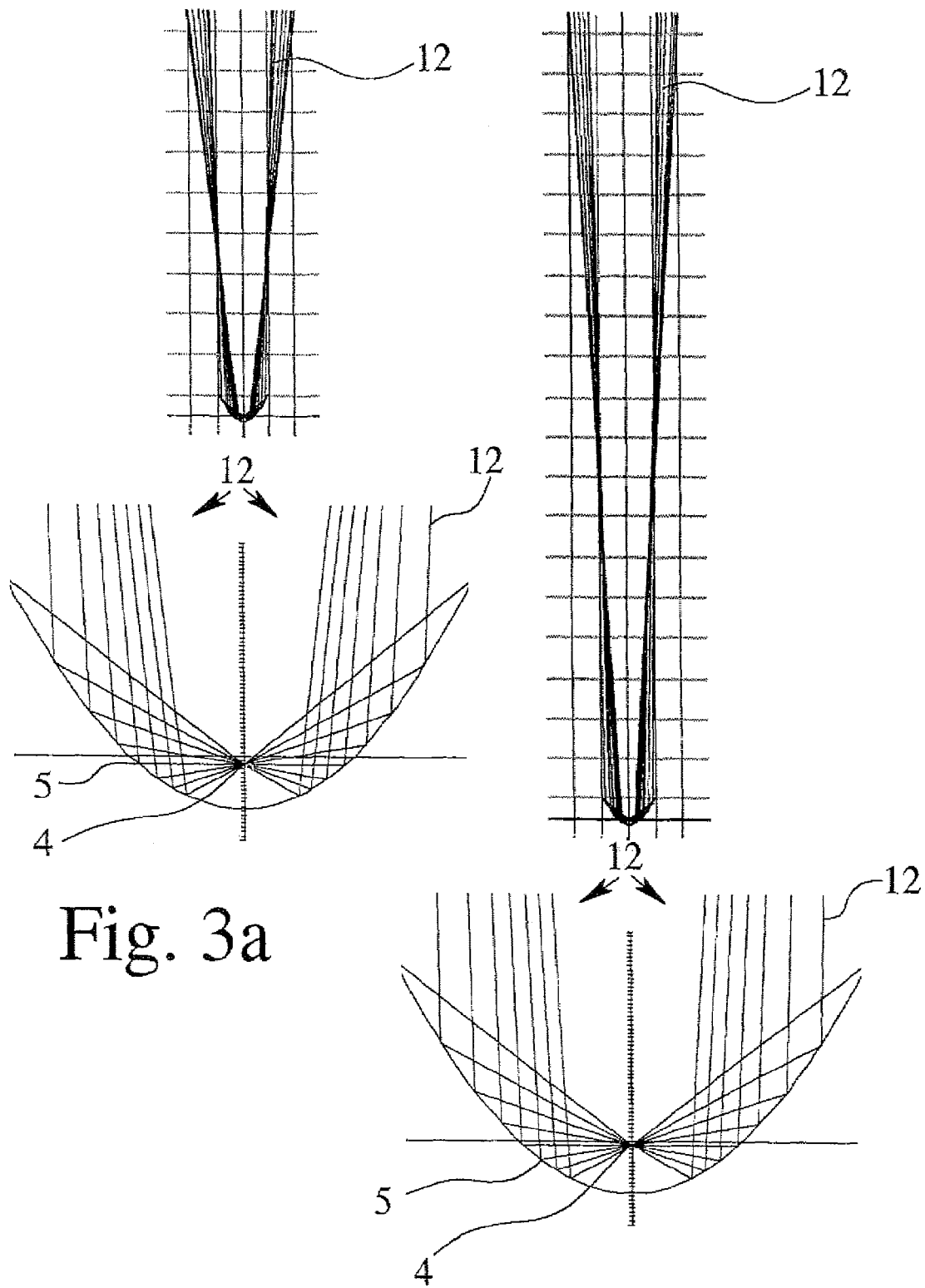
FIGS. 3a & 3b show the measurement beam paths which can be produced with the preferred exemplary embodiments of the analysis device in accordance with the invention.

In the optical analysis device 1 as shown in FIG. 1, the beam path of the measurement beam is adjustable, by which the illumination of the detectors 8, 9 can be influenced. In the analysis device shown in FIG. 1, the beam path of the measurement beam 12 is adjusted by moving the first radiation source 4 relative to the first reflector 5. FIGS. 3a & 3b show the action of displacement of the first radiation source 4 relative to the first reflector 5, the displacement here being limited to motion of the first radiation source 4 along the optical axis of the first reflector 5. FIGS. 3a & 3b, respectively, consist of a detailed view which documents the location of the first radiation source 4 relative to the first reflector 5, and of a representation of the resulting complete beam path of the measurement beam 12 which is shown developed.

When the first radiation source shown in FIG. 3a is moved out of the focal position in the direction to the first reflector 5, a widening of the path of the measurement beam 12 results; this adjustment would be used for comparatively short distances A of the external reflector 10 from the housing 2. In comparison, in FIG. 3b, the first radiation source 4 is rather near the focal point of the first reflector 5 and is deflected only slightly in the direction to the first reflector 5. This adjustment causes the path of the measurement beams 12 to be less spread, with the result that a measurement path which is much longer compared to FIG. 3a can be bridged until the same widening is achieved at the end of the illustrated beam path. The adjustment of the beam path of the measurement beam 12 as shown in FIG. 3b would be selected accordingly when the distance A of the external reflector 10 from the housing 2 is great.

Figure 4:
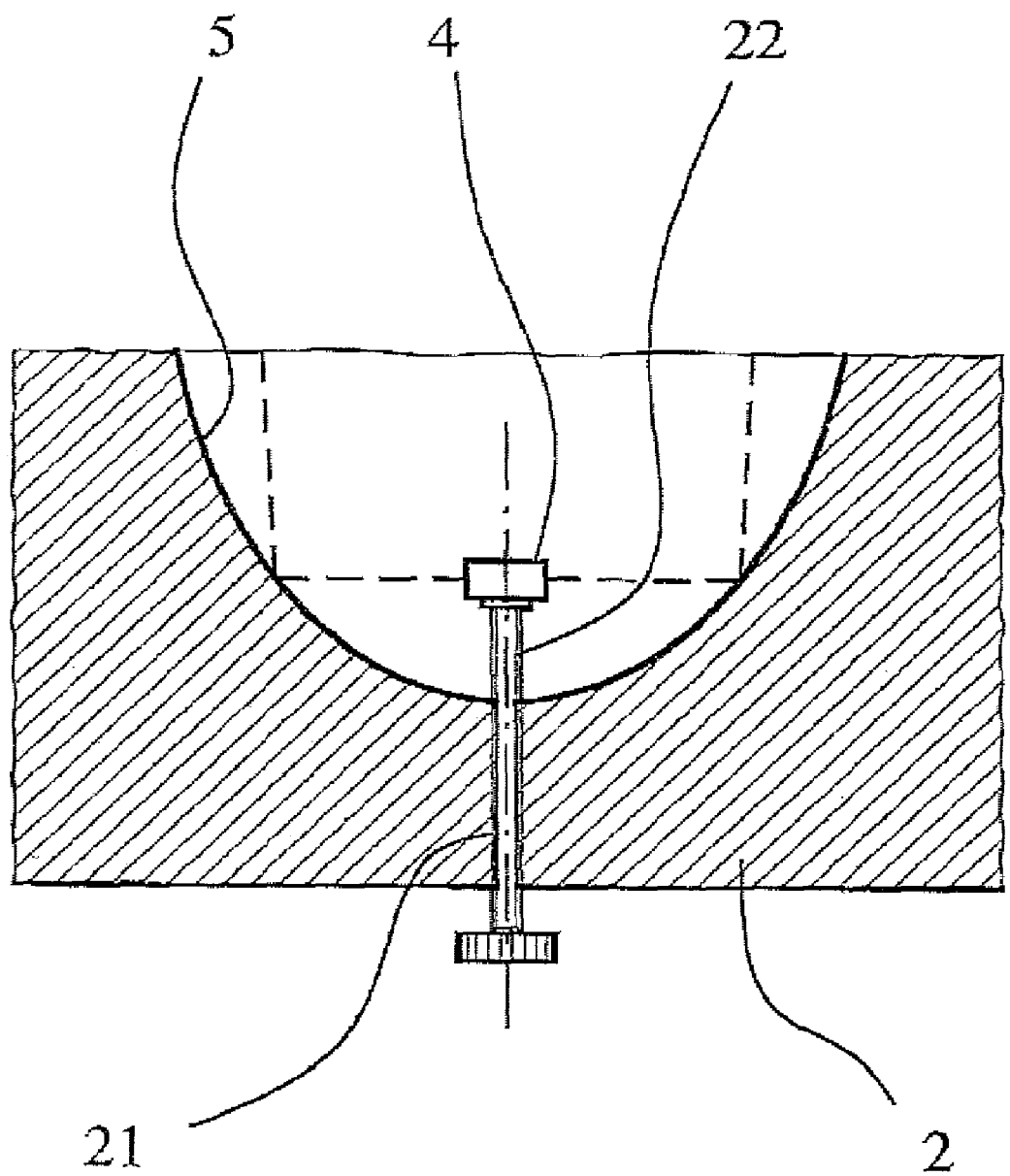
FIG. 4 is a view of the gaslight housing schematically depicting an arrangement for adjusting the position of the radiation source relative to the reflector.

FIG. 4 shows one of the various possible manners for producing adjustment of the beam path of the measurement beam 12. In this case, the first radiation source 4 is mounted on top of an adjustment screw that is screwed into a threaded opening 21 of the housing 2 and which has an adjustment knob on its outer end. By turning the screw 22, the screw 22, and with it the first radiation source 4, can be moved up and down relative to the first reflector 5.

In the analysis device in accordance with the invention, the absorption space can be open to the sides so that the substances to be studied can enter the absorption space 11 and can leave it again moving freely. In the preferred exemplary embodiment of an optical analysis device 1 which is shown in FIG. 1, the absorption space 11 is sealed off from the vicinity by a peripherally closed spacer 16 and is thus made as a closed measurement cell.

The housing 2 of the optical analysis device 1 shown in FIG. 1 is produced as an aluminum injection molding so that the reflecting surfaces provided in the housing 2, the surfaces of the first reflector 5, of the second reflector 7 and of the measurement beam reflector 14a, 14b are integral with the housing. The reflecting surfaces in this exemplary embodiment have been vapor coated with metal and have been polished. In another preferred exemplar embodiment (not shown), the housing, except for the radiation-permeable housing element, is made as a plastic injection molding which is coated to be highly reflective inside.

To prevent corrosion of the elements of the analysis device 1 located in the housing 2, the gastight housing 2 shown in FIG. 1 is filled with a protective gas. The protective gas also prevents the fogging of the optically active surfaces. In the illustrated exemplary embodiment, nitrogen has been used as the protective gas. Furthermore, the housing 2 of the optical analysis device 1 in FIG. 1 is filled with a gas which absorbs part of the radiation of the radiation sources 4, 5, with which the measurement properties of the analysis device 1 can be optimized.

In the preferred exemplary embodiments of the analysis device 1 in accordance with the invention, as shown in FIGS. 1 & 2, the first detector 8 and the second detector 9 are located in a common detector housing 18, optical filters 19, 20, being connected upstream of the detectors 8, 9, and likewise, being integrated into the detector housing 18. In the exemplary embodiment shown in FIG. 1, the optical filters 19, 20, are narrowband interference filters. The transmission range of the first interference filter 19 is in the absorption region of the substance to be detected and the transmission range of the second optical filter 20 is outside of possible absorption areas so that the radiation transmitted by it is not influenced by the absorption effects.

In the illustrated optical analysis devices 1, the radiation intensity of the radiation sources 4, 6, is electrically modulated with different frequencies. By demodulation of the signals detected by the detectors 8, 9, the corresponding signal portions traveling back to the first radiation source 4 and the second radiation source 6 can be recognized. A measurement value is generated by finding the quotient from the first detector 8 and from the second detector 9. This measurement value is a measure of the concentration of the substance to be detected. In this connection, it has been established to be advantageous if, for each detector 8, 9, the signal portion of the first radiation source 4 is referenced to the portion of the second radiation source 6. If the quotients formed in this way from the signal portions of the measurement beam 12 and of the reference beam 13 which have been detected by each individual detectors 8, 9, are referenced again to one another, the sole resulting total value is free of systematic changes in the radiation characteristic of the radiation sources 4, 6, and of changes of the detector and amplifier sensitivities.

In another preferred exemplary embodiment of an optical analysis device (not shown), the optical interfaces of the absorption space are additionally heated to prevent condensation.

What is claimed is:

1. Radiation absorption optical analysis device, comprising:
    a housing with at least one radiation-permeable housing element,
    at least a first radiation source in the housing,
    a first reflector assigned to the first radiation source in the housing,
    a second radiation source in the housing,
    a second reflector assigned to the second radiation source in the housing,
    at least a first detector in the housing,
    a second detector and
    an external reflector located outside the housing,
    an absorption space formed between the external reflector and the radiation-permeable housing element, and
    a measurement beam reflector in the housing,
    wherein measurement beams emitted by the first radiation source, after reflection by the first reflector, passing out of the housing to the external reflector, the emitted measurement beams being reflected by the external reflector to the measurement beam reflector in the housing after passing through the absorption space, and from the measurement beam reflector are directly directed onto the first detector and the second detector, and
    wherein reference beams emitted by the second radiation source are reflected by the second reflector and are directly directed onto the first detector and the second detector.

2. Optical analysis device in accordance with claim 1, wherein the measurement beam reflector is annular.

3. Optical analysis device in accordance with claim 2, wherein the measurement beam reflector is a segment of a paraboloid or spherical shell.

4. Optical analysis device in accordance with claim 1, wherein the measurement beam reflector has a surface that is configured to mix and homogenize the measurement beams so that measurement beams reflected from each region of the measurement beam reflector are distributed on the detectors.

5. Optical analysis device in accordance with claim 4, wherein the surface of the measurement beam reflector has at least one of a concave and a convex microstructuring.

6. Optical analysis device in accordance with claim 1, wherein a distance of the external reflector from the housing is adjustable.

7. Optical analysis device in accordance with claim 1, wherein the beam path of the measurement beams is adjustable.

8. Optical analysis device in accordance with claim 7, wherein the path of measurement beam is adjustable by shifting of the first radiation source relative to the first reflector.

9. Optical analysis device in accordance with claim 1, wherein surfaces of the reflectors in the housing have been surface-treated by at least one of galvanization, vapor coating, plasma coating and polishing.

10. Optical analysis device in accordance with claim 1, wherein the reflecting surfaces provided in the housing are integral portions of the housing, the housing being one of an injection molded part and a cast part.

11. Optical analysis device in accordance with claim 1, wherein the housing is filled with a protective gas.

12. Optical analysis device in accordance with claim 1, wherein the housing is filled with a gas which is able to absorb part of the radiation of the radiation sources.

13. Optical analysis device in accordance with claim 1, wherein the first detector and the second detector are located in a common detector housing.

14. Optical analysis device in accordance with claim 13, wherein the first detector and the second detector are one of pyroelectric detectors and thermopile detectors with optical filters being connected upstream of the detectors.

15. Optical analysis device in accordance with claim 14, wherein the optical filters are narrowband interference filters with a transmission range which lies in an absorption region of the substance to be detected.

16. Optical analysis device in accordance with claim 1, wherein optical interfaces of the absorption space are heated to avoid condensation.

* * * * *